United States Patent [19]

Kawamoto et al.

[11] Patent Number: 5,563,229
[45] Date of Patent: Oct. 8, 1996

[54] METHOD OF PRODUCING ORGANOPOLYSILOXANE WITH LOW POLYMERIZATION DEGREE

[75] Inventors: Hideyuki Kawamoto; Hisashi Aoki, both of Usui-gun, Japan

[73] Assignee: Shin-Etsu Chemical Co., Ltd., Tokyo, Japan

[21] Appl. No.: 463,785

[22] Filed: Jun. 5, 1995

[30] Foreign Application Priority Data

Sep. 5, 1994 [JP] Japan .................................. 6-235949

[51] Int. Cl.$^6$ .................................................. C08G 77/08
[52] U.S. Cl. ............................... 528/21; 528/37; 556/469
[58] Field of Search ........................ 528/21, 37; 556/469

[56] References Cited

U.S. PATENT DOCUMENTS

| | | | |
|---|---|---|---|
| 3,162,662 | 12/1964 | Brown et al. | 528/21 |
| 4,113,760 | 9/1978 | Frey et al. | 556/460 |
| 4,782,172 | 11/1988 | Niswonger et al. | 556/466 |

*Primary Examiner*—Melvyn I. Marquis
*Attorney, Agent, or Firm*—Millen, White, Zelano, & Branigan, P.C.

[57] ABSTRACT

There is provided a method of producing an organopolysiloxane with a low polymerization degree in a high yield, comprising a step of allowing a monochlorosilane represented by the following general formula (I) and hexamethylcyclotrisiloxane to undergo ring-opening reaction in the presence of a quaternary ammonium salt represented by the following general formula (II) and a step of hydrolyzing the reaction product:

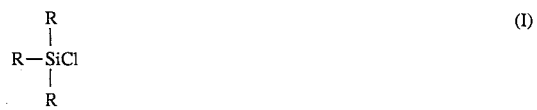

wherein R groups are the same or different, and each group represents an alkyl group containing 1 to 18 carbon atoms, an aryl group or a hydrogen atom;

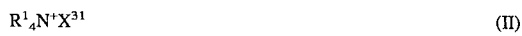

wherein $R^1$ groups are the same or different, each group representing an alkyl group containing 1 to 18 carbon atone, and X– represents an anion.

19 Claims, No Drawings

METHOD OF PRODUCING ORGANOPOLYSILOXANE WITH LOW POLYMERIZATION DEGREE

FIELD OF THE INVENTION

The present invention relates to a method of producing an organopolysiloxane with a low polymerization degree and, more particularly, to a method of selectively producing an organopolysiloxane with a low polymerization degree in a high yield by subjecting a monochlorosilane and hexamethylcyclotrisiloxane to a ring-opening reaction in the presence of a quaternary ammonium salt and then allowing the reaction product to undergo hydrolysis.

BACKGROUND OF THE INVENTION

As for the production of a dimethylpolysiloxane with a low polymerization degree (which is sometimes called "a dimethylpolysiloxane oligomer", hereinafter); there have so far been known the equilibration reaction between hexamethyldisiloxane and octamethylcyclotetrasiloxane in the presence of sulfuric acid as a catalyst (U.S. Pat. No. 2,469,888) and the method of using the simultaneous hydrolysis reaction of trimethylchlorosilane and dimethyldichlorosilane (U.S. Pat. No. 2,398,672).

However, those methods cannot produce an intended dimethylpolysiloxane oligomer alone in view of the characters of the reactions adopted therein, and so both yield and pot yield shown thereby are low. Further, it takes a long time to isolate the intended dimethylpolysiloxane oligomer alone from the reaction mixture by fractional distillation. Accordingly, they are at a disadvantage in entailing a high production cost.

Recently, the range of use of dimethylpolysiloxane oligomers has been increasing in various industrial fields, e.g., as cleaning agents for machine parts. In proportion thereto, requirements for reduction in the production cost of such oligomers and the steady supply thereof have been growing.

SUMMARY OF THE INVENTION

As a result of our intensive studies on selective, high-yield production of a dimethylpolysiloxane with a low polymerization degree, it has now been found that an intended dimethylpolysiloxane oligomer alone can be produced with a high yield when trimethylchlorosilane and hexamethylcyclotrisiloxane are subjected to ring-opening reaction in the presence of a quaternary ammonium salt and then to hydrolysis reaction. This method is advantageous in production cost and further applicable to the production of other polysiloxane oligomers wherein methyl groups of dimethylpolysiloxane oligomer are replaced by other alkyl groups or aryl groups, thereby achieving the present invention.

Therefore, an object of the present invention is to provide a method of selectively producing an organopolysiloxane with a low polymerization degree in a high yield.

The above-described object of the present invention is attained by allowing a monochlorosilane represented by the following general formula (I) and hexamethylcyclotrisiloxane to undergo ring-opening reaction in the presence of a quaternary ammonium salt represented by the following general formula (II), hydrolyzing the reaction product, and then isolating from the hydrolysis product an intended organopolysiloxane with a low polymerization degree in a purified condition:

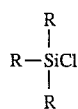

wherein R groups are the same or different, and each group represents an alkyl group containing 1 to 18 carbon atoms, an aryl group or a hydrogen atom;

wherein $R^1$ groups are the same or different each group representing an alkyl group containing 1 to 18 carbon atoms, and $X^-$ represents an anion.

DETAILED DESCRIPTION OF THE INVENTION

Specific examples of a monochlorosilane used in the present invention, which is represented by the foregoing general formula (I), include $Me_3SiCl$, $PhMe_2SiCl$, $C_{10}H_{21}Me_2SiCl$ and so on, but the invention should not be construed as being limited to these examples. In those chemical formulae, Me stands for a methyl group, and Ph a phenyl group (these representations will be used hereinafter, too).

As for the alkyl group containing 1 to 18 carbon atoms and the aryl group, no particular restriction is imposed thereon, as far as they don't spoil the effect of the present invention. However, a methyl group, an ethyl group and a decyl group are suitable examples of the alkyl group and a phenyl group is a suitable example of the aryl group.

Suitable examples of an anion represented by $X^-$ include $Cl^-$, $Br^-$, $I^-$, $HSO_4^-$ and $CH_3COO^-$.

The hexamethylcyclotrisiloxane used in the present invention has no particular limitation, but any of the commercially available ones are applicable to the present invention.

The amount of a monochlorosilane used, which is represented by general formula (I), is appropriately 2 to 20 times by equivalent as much as that of the hexamethylcyclotrisiloxane used. From the standpoints of yield and economical efficiency, it is particularly desirable that the amount be 3 to 10 times by equivalent, A quaternary ammonium salt used in the present invention, which is represented by the foregoing formula (II), functions as catalyst in the ring-opening reaction.

Specific examples of such a quaternary ammonium salt include $Bu_4N^+ Cl^-$, $Bu_4N^+ Br^-$, $(C_8H_{17})_3MeN^+ Cl^-$ and the like. Of these salts, $(C_8H_{17})_3MeN^+ Cl^-$ (trioctylmethylammonium chloride) is preferred over the others. In those formulae, Bu stands for a butyl group.

The proportion of the quantity of the quaternary ammonium salt used to the total weight of the monochlorosilane and the hexamethylcyclotri siloxane used (which is abbreviated as "the weight of silanes", hereinafter) is properly in the range of 0.01 to 5% by weight. From the economical point of view, however, it is desirable that the proportion be in the range of 0.3 to 2% by weight.

On the other hand, the proportion of the quantity of water used for the hydrolysis to the weight of silanes used is appropriately in the range of 30 to 300% by weight. From the standpoints of yield and pot yield, however, it is preferable for the proportion to range from 40 to 100% by weight.

Organopolysiloxanes with low polymerization degrees, which are the intended compounds of the present invention, are compounds represented by the following general formula (III):

wherein $R^2$, $R^3$ and $R^4$ groups are the same or different, and each group represents an alkyl group containing 1 to 18 carbon atoms, an aryl group or a hydrogen atom, and n is an integer.

Specifically, their examples are $Me(Me_2SiO)_4SiMe_3$ (corresponding to the compound of formula (III) wherein all of $R^2$, $R^3$ and $R^4$ groups are Me and n is 3), $Ph(Me_2SiO)_4SiMe_2Ph$ (corresponding to the compound of formula (III) wherein $R^2$ groups are Ph (phenyl groups), $R^3$ and $R^4$ groups are Me and n is 3), $Me(Me_2SiO)_7SiMe_3$ (corresponding to the compound of formula (III) wherein all of $R^2$, $R^3$ and $R^4$ groups are Me and n is 6) and so on.

For the organopolysiloxane with a low polymerization degree which is obtained using the present method, it is preferable to have a molecular weight of no greater than 1,500 from the standpoint of easy purification, e.g., through molecular distillation.

The production method of the present invention is embodied by allowing a monochlorosilane represented by general formula (I) and hexamethylcyclotrisiloxane to undergo ring-opening reaction, hydrolyzing the reaction product, and then, from the reaction mixture obtained, isolating and purifying the intended organopolysiloxane with a low polymerization degree. Herein, the ring-opening reaction is effected by refluxing the monochlorosilane-hexamethylcyclotrisiloxane mixture under an atmosphere of nitrogen. The temperature at which the ring-opening reaction is carried out is desirably in the range of 20° C. to 70° C. From the standpoint of reduction in the amount of a catalyst used, however, the temperature range of 40° C. to 70° C. is advantageous to the ring-opening reaction.

The hydrolysis reaction can be effected by dropping the reaction solution obtained into water under ordinary or reduced pressure. Additionally, the yield can be improved by removing the hydrogen chloride gas produced upon hydrolysis from the reaction system.

The appropriate temperature during the hydrolysis reaction is in the range of 0° to 50° C. In order to inhibit the decomposition of Si—Cl bond by the hydrochloric acid produced, however, it is desirable that the temperature be in the range of 5° to 25° C. As for the dropping speed, setting it as slow as possible is advantageous in view of ensuring a high yield. From the economical point of view, however, it is desirable to drop the reaction solution at a speed of 0.3 to 2.0 g/min.

In accordance with the production method of the present invention, an intended organopolysiloxane with a low polymerization degree can be selectively obtained in a high yield.

The present invention will be illustrated by the following examples which are not to be considered as limiting on or determinative of the scope of this invention.

EXAMPLE 1

$Me_3SiCl$ (71 g, 0.66 mole), hexamethylcyclotrisiloxane (23 g, 0.11 mole) and trioctylmethylammonium chloride (0.28 g, $0.7\times10^{-3}$ mole) were put in a 200 ml flask, and refluxed for 6 hours under an atmosphere of nitrogen.

Under a room temperature of 20° C., the reaction solution obtained was dropped into 56 g of water placed in a 500 ml of flask over a one-hour period with vigorous stirring, thereby effecting the hydrolysis. After the dropping was completed, the reaction solution was washed with 56 g each of water for 6 times to adjust the pH thereof to 7, and then subjected to vacuum distillation. Thus, 29.5 g of a dimethylpolysiloxane oligomer of the formula, $Me_3SiO(Me_2SiO)_3SiMe_3$, was obtained (in 70% yield).

EXAMPLE 2

$Me_3SiCl$ (71 g, 0.66 mole), hexamethylcyclotrisiloxane (23 g, 0.11 mole) and trioctylmethylammonium chloride (0.28 g, 0.70 millimole) were put in a 200 ml flask, and refluxed for 6 hours under an atmosphere of nitrogen.

Then, the excess $Me_3SiCl$ was distilled away at 70° C. under reduced pressure of 20 mmHg, and the residue obtained was dropped into 56 g of water placed in a 500 ml of flask under a temperature not higher than 20° C. over a one-hour period with vigorous stirring, thereby effecting the hydrolysis. After the hydrolysis was completed, the reaction solution was washed with 56 g each of water for 6 times to adjust the pH thereof to 7, and then subjected to vacuum distillation. Thus, 13.3 g of a dimethylpolysiloxane oligomer of the formula, $Me_3SiO(Me_2SiO)_6SiMe_3$, was obtained (in 40% yield).

COMPARATIVE EXAMPLE 1

Hexamethyldisiloxane (100 g, 0.62 mole) and octamethylcyclotetrasiloxane (137 g, 0.46 mole) and 7.1 g of concentrated sulfuric acid were put in a 300 ml flask, and underwent the equilibration reaction for 8 hours under a room temperature of 20 t. Thereafter, the reaction solution was washed with 100 g each of water for 6 times to adjust the pH thereof to 7, and then subjected to vacuum distillation. Thus, 23.7 g of a dimethylpolysiloxane oligomer of the formula, $Me_3SiO(Me_2SiO)_3SiMe_3$, was obtained (in 10% yield).

COMPARATIVE EXAMPLE 2

A solution containing $Me_3SiCl$ (47 g, 0.44 mole) and $Me_2SiCl_2$ (83.6 g, 0.65 mole) was admixed with water (314 g, 17.4 mole) to undergo hydrolysis. The resulting solution was washed with 100 g each of water for 6 times so as to adjust the pH thereof to 7, and then subjected to vacuum distillation. Thus, 8.5 g of a dimethylpolysiloxane oligomer of formula, $Me_3SiO(Me_2SiO)_3SiMe_3$, was obtained (in 10% yield).

What is claimed is:

1. A method of producing an organopolysiloxane with a low polymerization degree, comprising a step of allowing a monochlorosilane represented by the following general formula (I) and hexamethylcyclotrisiloxane to undergo ring-opening reaction in the presence of a quaternary ammonium salt represented by the following general formula (II) to form a reactant solution and a step of hydrolyzing the reaction product by dropping the reaction solution into water and removing the produced hydrogen chloride gas:

wherein R groups are the same or different, and each group represents an alkyl group containing 1 to 18 carbon atoms, an aryl group or a hydrogen atom;

$$R^1_4N^+X^- \qquad (II)$$

wherein $R^1$ groups are the same or different, each group represents an alkyl group containing 1 to 18 carbon atoms, and $X^-$ represents an anion.

2. A method of producing an organopolysiloxane with a low polymerization degree as claimed in claim 1, wherein the monochlorosilane is trimethylchlorosilane, phenyldimethylchlorosilane or decyldimethylchlorosilane.

3. A method of producing an organopolysiloxane with a low polymerization degree as claimed in claim 1, wherein the quaternary ammonium salt is trioctylmethylammonium chloride.

4. A method of producing an organopolysiloxane with a low polymerization degree as claimed in claim 1, wherein the monochlorosilane is used in an amount 2 to 20 times by equivalent to the amount of hexamethylcyclotrisiloxane used.

5. A method of producing an organopolysiloxane with a low polymerization degree as claimed in claim 1, wherein the organopolysiloxane produced is an organopolysiloxane having a molecular weight not higher than 1,500.

6. A method of producing an organopolysiloxane with a low polymerization degree as claimed in claim 1, wherein the organopolysiloxane produced is dodecamethylpentasiloxane or octadecamethyloctasiloxane.

7. A method of producing an organopolysiloxane with a low polymerization degree as claimed in claim 1, wherein the quaternary ammonium salt is used in a quantity of from 0.01 to 5% based on the total weight of the monochlorosilane and the hexamethylcyclotrisiloxane used.

8. A method of producing an organopolysiloxane with a low polymerization degree as claimed in claim 5, wherein the quaternary ammonium salt is used in a quantity of from 0.01 to 5% based on the total weight of the monochlorosilane and the hexamethylcyclotrisiloxane used.

9. A method of producing an organopolysiloxane with a low polymerization degree as claimed in claim 6, wherein the quaternary ammonium salt is used in a quantity of from 0.01 to 5% based on the total weight of the monochlorosilane and the hexamethylcyclotrisiloxane used.

10. A method of producing an organopolysiloxane with a low polymerization degree as claimed in claim 1, wherein the hydrolyzing step uses water in a quantity of from 40 to 100% based on the total weight of the monochlorosilane and the hexamethylcyclotrisiloxane used.

11. A method of producing an organopolysiloxane with a low polymerization degree as claimed in claim 1, wherein the ring-opening reaction is carried out under reflux in an atmosphere of nitrogen.

12. A method of producing an organopolysiloxane with a low polymerization degree as claimed in claim 11, wherein the ring-opening reaction is carried out at a temperature of from 20° to 70° C.

13. A method of producing an organopolysiloxane with a low polymerization degree as claimed in claim 1, wherein the step of hydrolyzing the reaction product is carried out by dropping the reaction solution into water as the hydrolysis temperature is kept at 5° to 25° C.

14. A method of producing an organopolysiloxane with a low polymerization degree as claimed in claim 13, wherein the dropping speed of the reaction solution is in the range of 0.3 to 2.0 g/min, 15. The method of claim 1, wherein, in formula (I), each R group is the same or different and represents methyl, ethyl, decyl or phenyl and, in formula (II), each $R^1$ group is the same or different and represents methyl, ethyl or decyl.

16. The method of claim 1, wherein, in formula (II), X is $Cl^-$, $Br^-$, $I^-$, $HSO_4^-$, or $CH_3COO^-$.

17. The method of claim 1, wherein the monochlorosilane is used in an amount of 3 to 10 times by equivalent to the amount of hexamethylcyclotrisiloxane.

18. The method of claim 1, wherein the quaternary ammonium salt is $Bu_4N^+Cl^-$, $Bu_4N^+Br^-$ or $(C_8H_{17})_3MeN^+Cl^-$.

19. The method of claim 1, wherein the organopolysiloxane with a low polymerization degree reaction product has a molecular weight no greater than 1,500.

* * * * *